United States Patent
Schonholz et al.

(10) Patent No.: US 9,089,312 B2
(45) Date of Patent: Jul. 28, 2015

(54) TAMPONADE FOR BIOPSY SURGERY AND METHOD OF OPERATION

(75) Inventors: Steven Michael Schonholz, Warren, MA (US); Robert T. T. Gettens, Longmeadow, MA (US); Allison Waller, Milford, MA (US)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 185 days.

(21) Appl. No.: 13/413,005

(22) Filed: Mar. 6, 2012

(65) Prior Publication Data

US 2012/0232581 A1 Sep. 13, 2012

Related U.S. Application Data (60) Provisional application No. 61/451,183, filed on Mar. 10, 2011.

(51) Int. Cl.
| | | |
|---|---|---|
| A61B 17/08 | (2006.01) | |
| A61D 1/00 | (2006.01) | |
| A61B 17/00 | (2006.01) | |
| A61M 25/10 | (2013.01) | |
| A61B 10/02 | (2006.01) | |

(52) U.S. Cl.
CPC .......... *A61B 17/0057* (2013.01); *A61M 25/10* (2013.01); *A61B 10/0275* (2013.01); *A61B 2017/00641* (2013.01); *A61B 2017/00654* (2013.01); *A61M 2025/1081* (2013.01)

(58) Field of Classification Search
CPC ............. A61B 17/0057; A61B 17/12136; A61B 17/1215; A61B 17/00641; A61B 17/00654; A61B 10/0275; A61M 29/00; A61M 25/10

USPC ......... 606/190, 191, 192, 193, 194, 195, 196, 606/197, 198, 199, 213; 604/96.01, 604/103.01–103.05, 104–109

See application file for complete search history.

(56) References Cited

U.S. PATENT DOCUMENTS

| | | | |
|---|---|---|---|
| 5,779,698 A * | 7/1998 | Clayman et al. ................. 606/39 |
| 6,368,341 B1 * | 4/2002 | Abrahamson ................. 606/213 |
| 6,706,051 B2 * | 3/2004 | Hudson et al. ................. 606/196 |
| 7,824,675 B2 | 11/2010 | Ni et al. |
| 7,828,810 B2 | 11/2010 | Liddicoat et al. |
| 7,838,636 B1 | 11/2010 | Ruben et al. |
| 7,846,168 B2 | 12/2010 | Liddicoat et al. |
| 7,846,706 B2 | 12/2010 | Mintier et al. |
| 7,847,079 B2 | 12/2010 | Rosen et al. |
| 7,850,963 B2 | 12/2010 | Rosen et al. |
| 7,857,626 B2 | 12/2010 | Toly |
| 7,862,818 B2 | 1/2011 | Roschke et al. |
| 7,888,466 B2 | 2/2011 | Li |
| 2003/0073979 A1 * | 4/2003 | Naimark et al. ........... 604/891.1 |
| 2005/0020899 A1 * | 1/2005 | Chernomorsky et al. ..... 600/407 |
| 2008/0086109 A1 * | 4/2008 | Shabty et al. ................. 604/508 |
| 2009/0112239 A1 * | 4/2009 | To ................................. 606/159 |

* cited by examiner

*Primary Examiner* — Katrina Stransky
(74) *Attorney, Agent, or Firm* — Cantor Colburn LLP (57) ABSTRACT

A device for a biopsy procedure using a probe is provided. The probe, such as a needle, has an inner bore. A tamponade device is provided having a stem portion and an expandable portion, the tamponade device is sized to fit within the probe inner bore. The expandable portion is changeable between a first size and a second size with the second size being larger than the first size. A sheath disposed about the expandable portion, the sheath sized to fit within the probe inner bore. The expandable portion applies direct pressure to a hemorrhage location when inflated to the second size.

9 Claims, 11 Drawing Sheets

TAMPONADE FOR BIOPSY SURGERY AND METHOD OF OPERATION

CROSS REFERENCE TO RELATED APPLICATIONS

The present application claims the benefit of U.S. Provisional Application Ser. No. 61/451,183, filed Mar. 10, 2011, the contents of which is incorporated by reference herein.

BACKGROUND OF THE INVENTION

The subject matter disclosed herein relates to a tamponade and a method of controlling a hemorrhage, and in particular to a tamponade for controlling a hemorrhage that occurs during a vacuum assisted percutaneous core breast biopsy.

Figure 1:
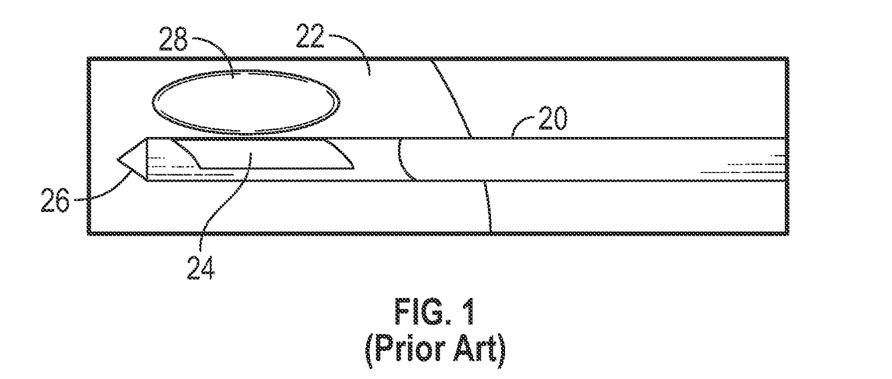
FIG. 1 is a prior art needle being inserted during a vacuum assisted percutaneous core breast biopsy procedure.
Figure 2:
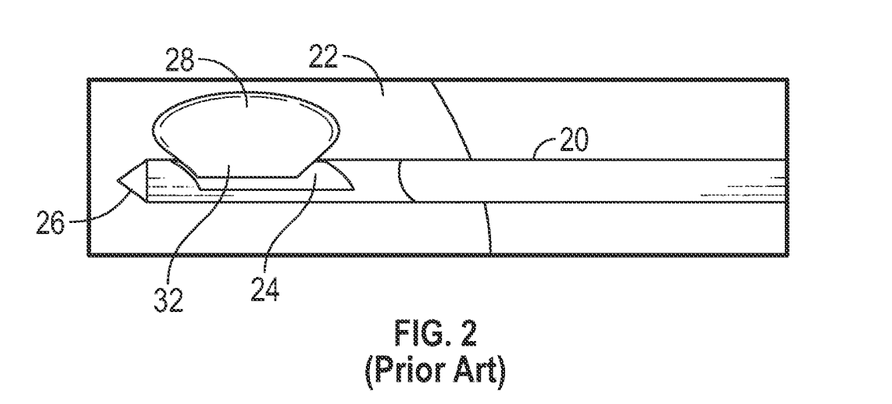
FIG. 2 is the needle of FIG. 1 drawing a sample from a lesion.
Figure 3:
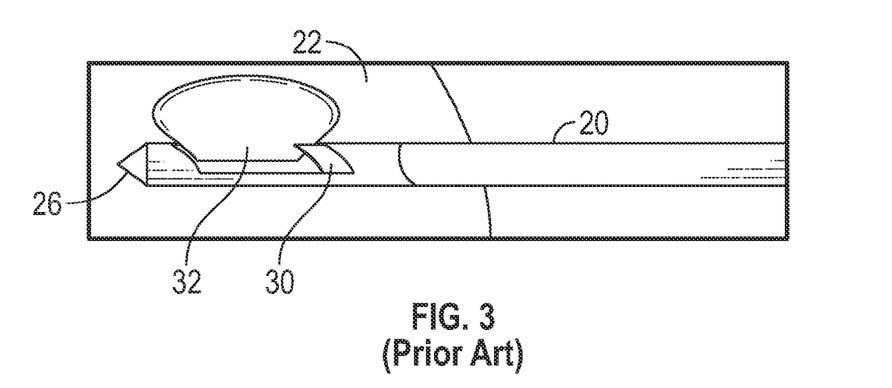
FIG. 3 is the needle of FIG. 1 cutting the sample from the lesion.

Vacuum assisted breast biopsy (VABB) is a method used to remove breast tissue that has been identified as suspicious on a mammogram, ultrasound, magnetic resonance imaging (MRI), or physical exam. It allows the tissue to be examined and identified as benign or cancerous. When performing this type of biopsy, a large probe or needle 20 is inserted into the breast 22 under radiological guidance as shown in FIGS. 1-3. In a VABB procedure, an aperture 24 near the tip 26 the needle 20 positioned directly into the lesion 28 or directly inferior to it (FIG. 1). Once the needle 20 has been positioned, a vacuum is applied to an inner bore of the needle 20 to draw the lesion 28 into the aperture 24 (FIG. 2) and a cutting mechanism 30 cuts a sample 32 from the lesion 28 (FIG. 3). This sample 32 is then transported to the distal end of the needle 20 by the vacuum, removed, and retained for testing. Once the sample 32 has been removed, the needle 20 is rotated or elevated and the process is repeated until the lesion 28 or the desired amount of samples have been removed.

It is estimated that up to 7% of patients who undergo a VABB procedure experience a hemorrhage condition during the procedure. To stop the bleeding in these patients, the surgeon or technician removes the needle 20 and applies exterior pressure to the breast 22. The application of external pressure does not allow the physician to apply pressure directly to the hemorrhage site that is located within the incision created during the procedure. In some cases, the hemorrhage cannot be controlled using this method and surgery is required. It should be appreciated that it is undesirable to perform surgery on a patient that has not fasted prior to the procedure due to the risk of complications.

While existing biopsy procedures and methods of controlling hemorrhages are suitable for their intended purposes the need for improvement remains, particularly in providing a device that can stop the bleeding from a hemorrhage safely, effectively, easily and quickly during a surgical procedure.

BRIEF DESCRIPTION OF THE INVENTION

According to one aspect of the invention, a tamponade device for a biopsy procedure using a probe with an inner bore is provided. The tamponade device includes a stem portion sized to fit within the inner bore. An expandable portion is sized to fit within the inner bore, the expandable portion changeable between a first size and a second size wherein the second size is larger than the first size. A sheath sized to fit within the inner bore is disposed about the expandable portion.

According to another aspect of the invention, a device for use with a biopsy procedure is provided. The device includes a tamponade having a stem portion with and inner bore and an expandable portion, the expandable portion having a substantially hollow interior in fluid communication with the inner bore and having an outer surface. The expandable portion is inflatable from a first size to a second size, wherein the second size is larger than the first size. A sheath is provided having an inner portion and an outer surface, the sheath being disposed over and removably coupled to the outer surface, wherein the sheath is made from a biocompatible and biodegradable material. A surgical sealant is disposed on the outer surface of the sheath.

According to yet another aspect of the invention, a method of stopping hemorrhaging during a biopsy procedure is provided. A probe having an aperture in a proximal end and a inner bore extending between the proximal end and a distal end is inserted. A tamponade is inserted into the inner bore at the distal end, the tamponade having a stem portion, an expandable portion and a sheath disposed about the expandable portion. The tamponade is moved through the aperture. The probe is removed. The expandable portion is increased from a first size to a second size. The size of the expandable portion is reduced and removed.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Embodiments of the present invention relate to a tamponade device that provides advantages in reducing the amount of time to stop bleeding of hemorrhaging during a vacuum assisted breast biopsy (VABB) procedure. The tamponade device may provide further advantages being quickly applied to the location of the hemorrhaging internal to the breast. The tamponade mechanism provides advantages to the medical personnel by allowing them to apply internal pressure directly to the hemorrhaging site. The tamponade may allow direct pressure to the hemorrhaging area with enough pressure to overcome venous or arterial pressure. The tamponade may provide advantages in eliminating or reducing the use of external pressure to the breast during a hemorrhage. The tamponade device may provide further advantages in increasing patient comfort, decreasing the amount of bruising and reducing the need for surgery.

Figure 4:
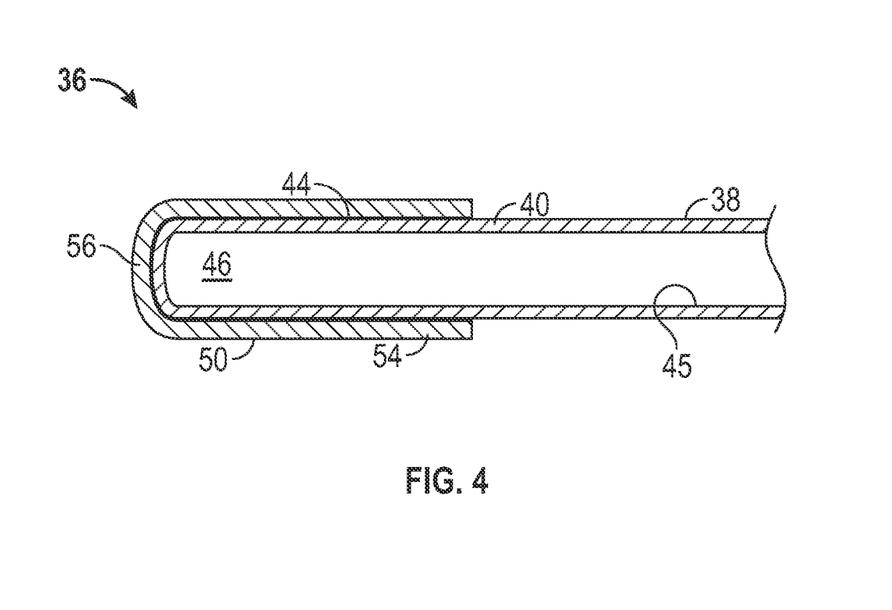
FIG. 4 is a partial side sectional view of a tamponade device in accordance with an embodiment of the invention.
Figure 5:
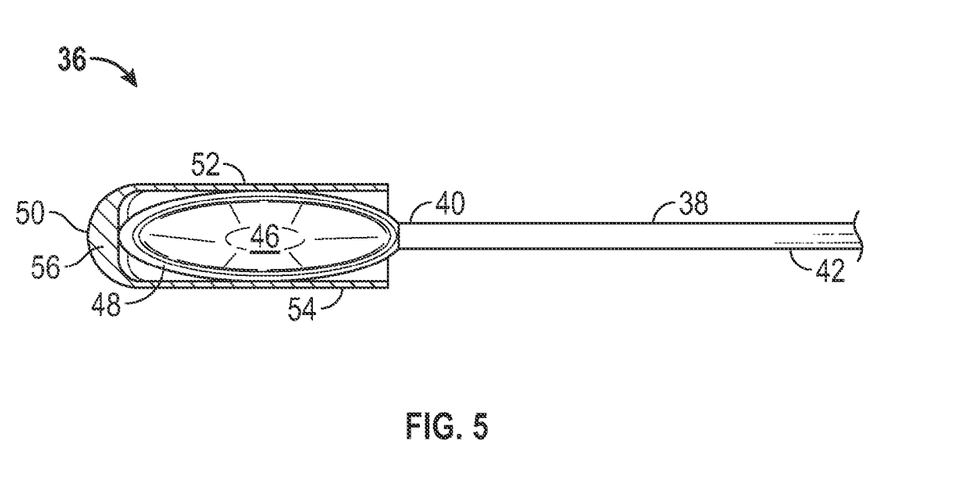
FIG. 5 is a partial side sectional view of the tamponade device of FIG. 4 in a partially inflated position.

Referring to FIGS. 4-5, is a tamponade device 36 in accordance with an exemplary embodiment. The tamponade device 36 includes a stem portion 38 having a proximal end 40 and a distal end 42. The stem portion 38 is a generally thin walled member having an inner bore 45. The inner bore 45 is open on the distal end and configured to receive a pressurized fluid such as air or saline for example. In the exemplary embodiment, the stem portion 38 has an outer diameter of 1.8 millimeters and an inner diameter of 1.4 millimeters. The stem portion may be made from a suitable biocompatible material such as Nylon 6,6 for example. In one embodiment, the stem portion 38 is made from a material that is visible by MRI, ultrasound and mammography imaging devices.

Extending from the proximal end 40 is an expandable portion 44. The expandable portion 44 has a hollow interior area 46 that is in fluid communication with the inner bore 44. The expandable portion 44 includes an outer surface 48. The expandable portion has a length of about 11 millimeters. As will be discussed in more detail below, during operation, the expandable portion may be inflated from a first size to a second size. In the exemplary embodiment, the expandable portion has a diameter of about 2.0 millimeters in the deflated state and a diameter of about 20 millimeters in the inflated state. The expandable portion 44 is made from a suitable biocompatible material such as polyethylene-terephthalate, polyurethane or polydimethyl-siloxane for example. In one embodiment, the expandable portion 44 is capable of withstanding a pressure corresponding to double a normal systolic blood pressure level to halt the flow of blood in patients having elevated blood pressure. In one embodiment, the expandable portion 44 may withstand a pressure of about 1000 mmHg for an extended period of time, such as 12 hours for example. In the exemplary embodiment, the expandable portion 44 and stem portion 38 are molded as a single contiguous and integral member. In one embodiment, the expandable portion 44 is a 20 mm×10 mm WorkHorse® II PTA balloon catheter manufactured by AngioDynamics Inc.

Figure 12:
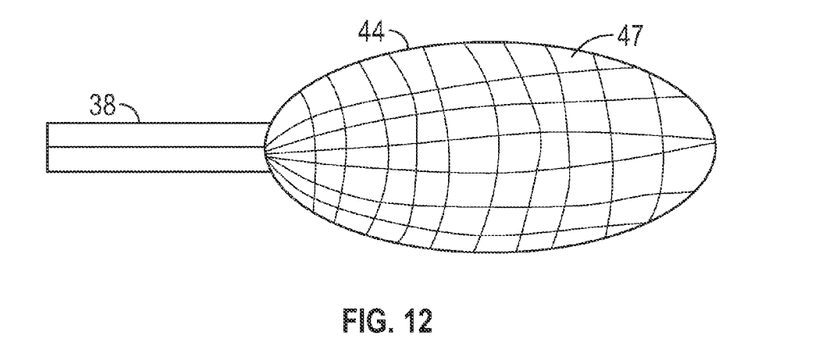
FIG. 12 illustrates an embodiment for the balloon end of the tamponade device of FIG. 4.
Figure 13:
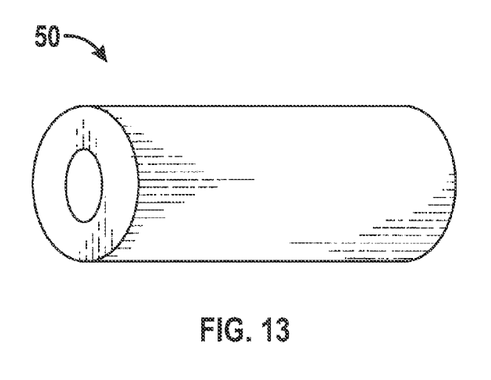
FIG. 13-15 illustrate different embodiments for a sheath that may be used on the tamponade device of FIG. 4.

In one embodiment shown in FIG. 12, the balloon 44 includes a plurality of cautery wires 47 disposed about the periphery of the balloon 44. In this embodiment, after the balloon 44 is inflated, the cautery is energized and the area within the cavity is cauterized. Once the cauterization is complete, the balloon 44 and cautery wires 47 may be removed.

Disposed about the outer surface 48 is a sheath 50. The sheath 50 is made from biodegradable and bioabsorbable material such as copoly lactic acid/glycolic acid for example. In one embodiment, the sheath 50 includes a relatively thin wall area 54 adjacent the side wall of the expandable portion and a thicker wall area 56 on a distal end. As will be discussed in more detail below, the sheath 50 increases in size when the expandable portion is inflated. The increase in size forces the sheath 50 into contact with the hemorrhage location within the incision of the patient. Thus, the sheath 50 performs the function of a bandage to stop the flow of blood. The sheath 50 may include a weaved dressing, a polymeric dressing or a gel-material dressing for example. In one embodiment, the sheath 50 includes a surgical sealant material disposed on the outer surface 52 to ensure that the sheath 50 adheres to the surrounding tissue.

Figure 14:
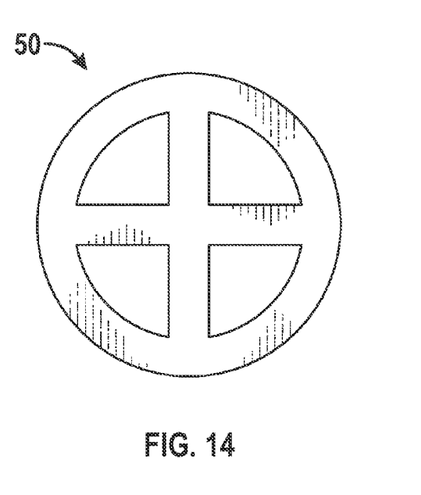
Figure 15:
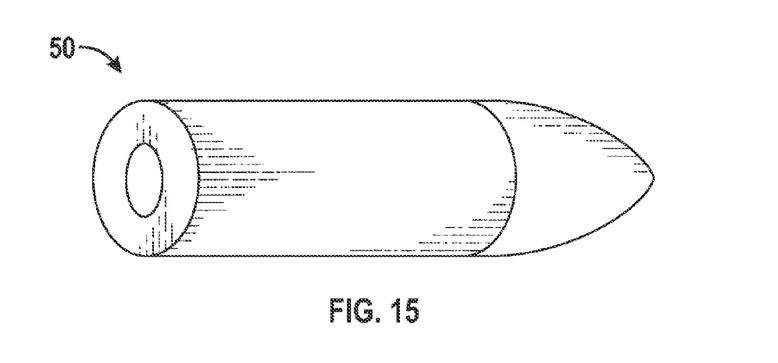
Figure 16:
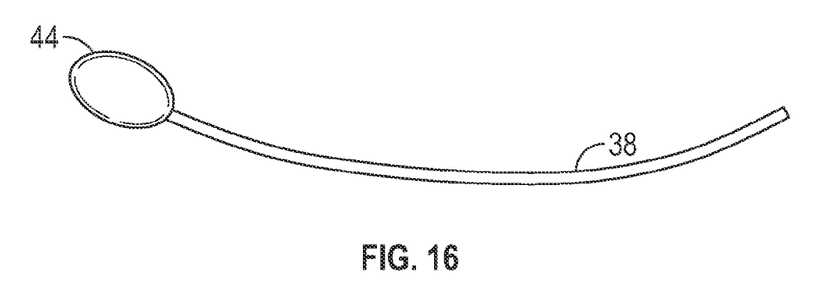
FIG. 16-21 illustrate different embodiments for deploying the balloon end of the tamponade device of FIG. 4.

The sheath 50 may be constructed with several different shapes as is shown in FIGS. 4-5 and FIGS. 13-15. The sheath 50 may have a spherical or partially spherical end (FIGS. 4-5). The sheath 50 may be cylindrical with a flat closed end (FIG. 13), or cylindrical with a partially open end (FIG. 14). The sheath 50 may also be "bullet" shaped having a curved pointed end (FIG. 15). It should be appreciated that the sheaths described herein are for exemplary purposes and the claimed invention should not be so limited.

In one embodiment, the tamponade device 36 including the stem portion 38, the expandable portion 44 and the sheath 50 are made of materials visible by MRI, ultrasound, and mammography imaging devices. In another embodiment, the materials of the stem portion 38 and expandable portion 44 are selected to survive 24 hours without degradation after insertion into the breast 22. In another embodiment, the sheath 50 may survive 24 hours to one week, and preferably 48 hours before degradation begins.

Figure 6:
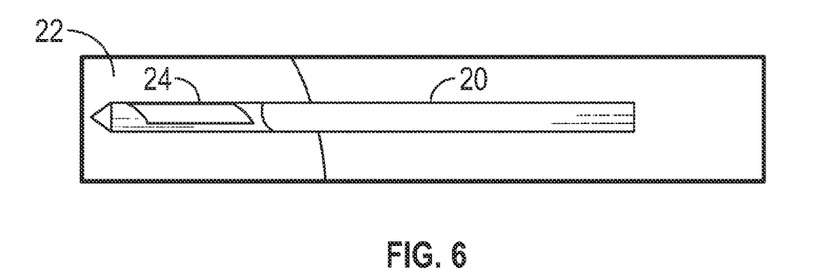
FIG. 6-11 are a partial side sectional view of a breast biopsy procedure using the tamponade device of FIG. 4.
Figure 7:
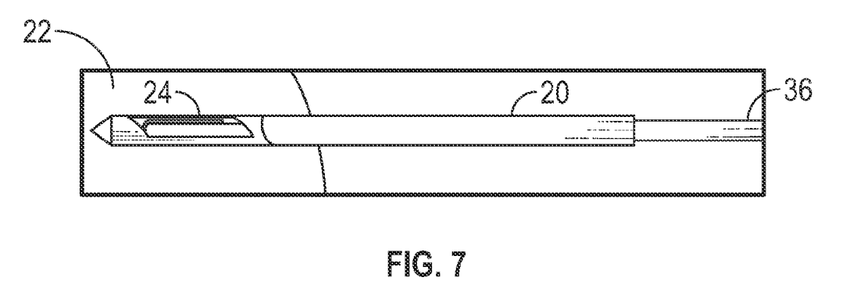

Referring now to FIGS. 6-11 an exemplary method of using the tamponade device 36 will be described. The method to stop hemorrhage utilizes a tamponade device 36 which is inserted through the probe 20 and into the breast tissue 22 via the same passage or bore through which the tissue samples 32 are transported. The aperture 24 on the proximal end 26 of the probe 20 will already be positioned at the site of hemorrhage (FIG. 6). The tamponade device are inserted through the distal end of the probe 20 (FIG. 7) and guided through to the aperture 24.

Once in position, the tamponade device 36 is advanced through the aperture 24. The tamponade device 36 may exit the needle 20 using a variety of embodiments as illustrated in FIGS. 16-21. The stem portion 38 may be curved (FIG. 16) placing one side of the stem portion 38 in tension such that when the balloon 44 reaches the aperture 24, the tension in the stem portion 38 biases the balloon out of the needle 20.

Figure 17:
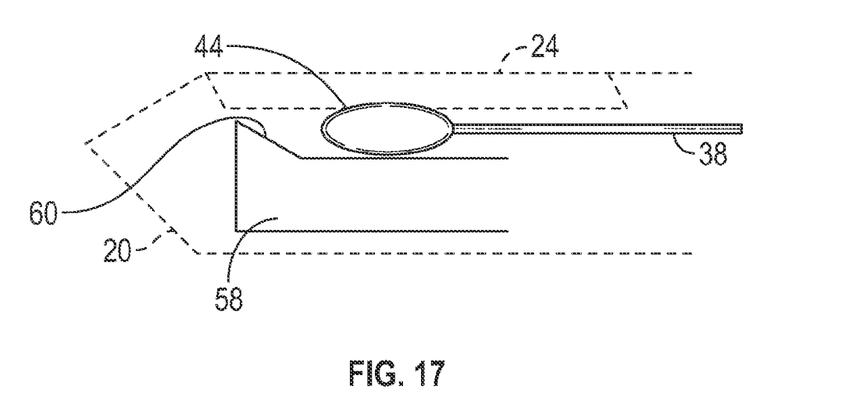
Figure 18:
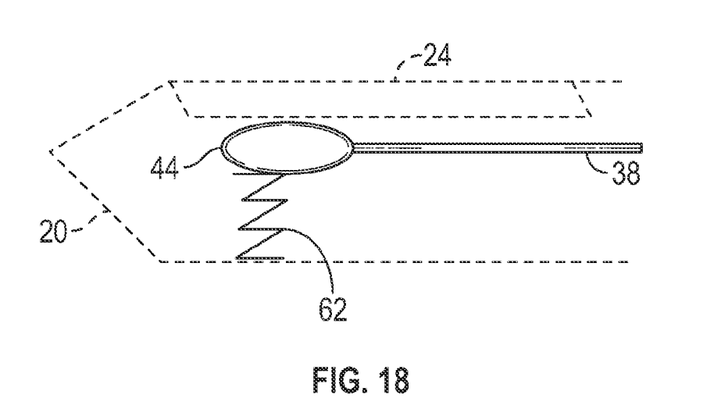

In other embodiments, a feature or device may be arranged to bias the balloon 44 adjacent the aperture 24. The needle 20 may include a ramp 58 having an angled surface 60 (FIG. 17). In this embodiment, as the balloon 44 is advanced through the needle 20, the balloon 44 contacts the surface 60 which redirects the path of travel through the aperture 24. In another embodiment, a biasing member such as spring 62 is coupled to the balloon 44. When the balloon 44 is inserted into the stem portion 38, the spring 62 is compressed, which bias' the balloon 44 towards one side of the needle 20. As the balloon 44 reaches the end of the needle 20, the tension in the spring 62 bias' the balloon 44 through the aperture 24.

Figure 19:
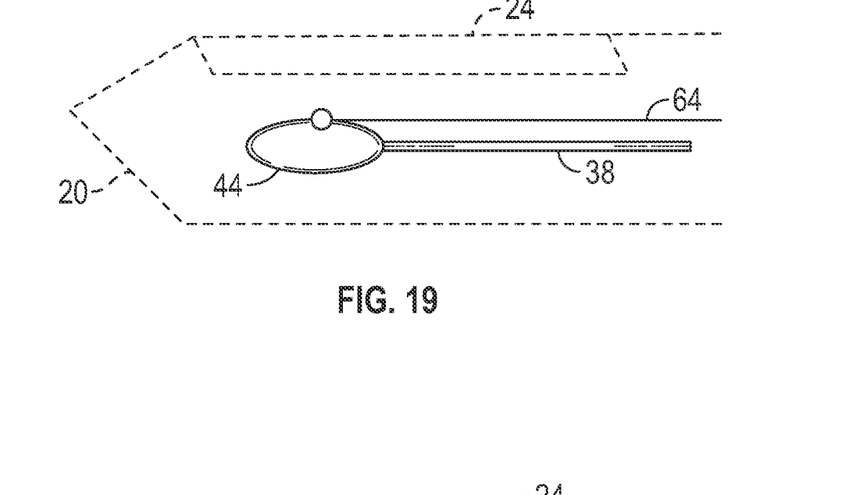
Figure 20:
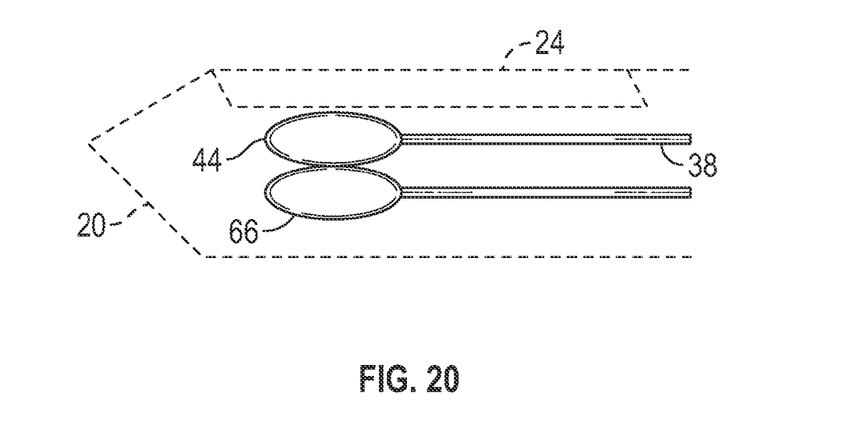
Figure 21:
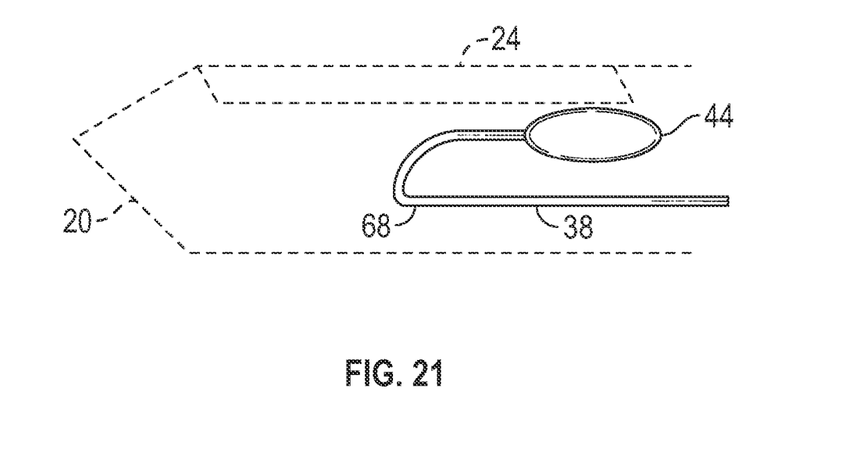
Figure 22:
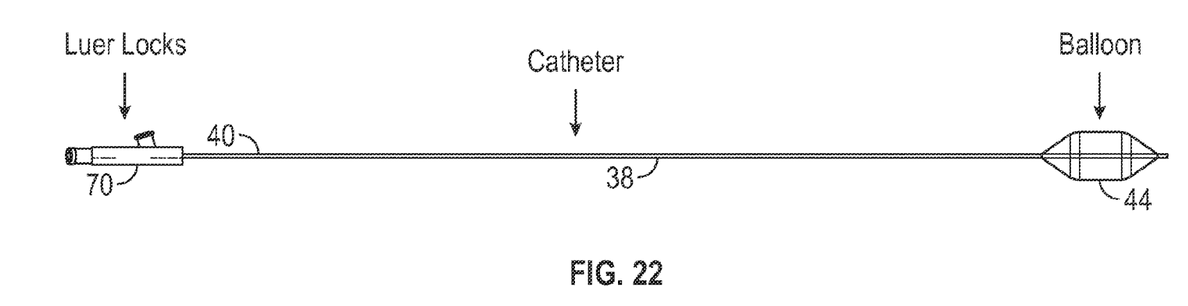
FIG. 22-26 illustrate an embodiment having a luer lock on one end of the catheter; and, FIG. 27-29 illustrate an embodiment wherein the tamponade device is packaged as a kit.
Figure 23:
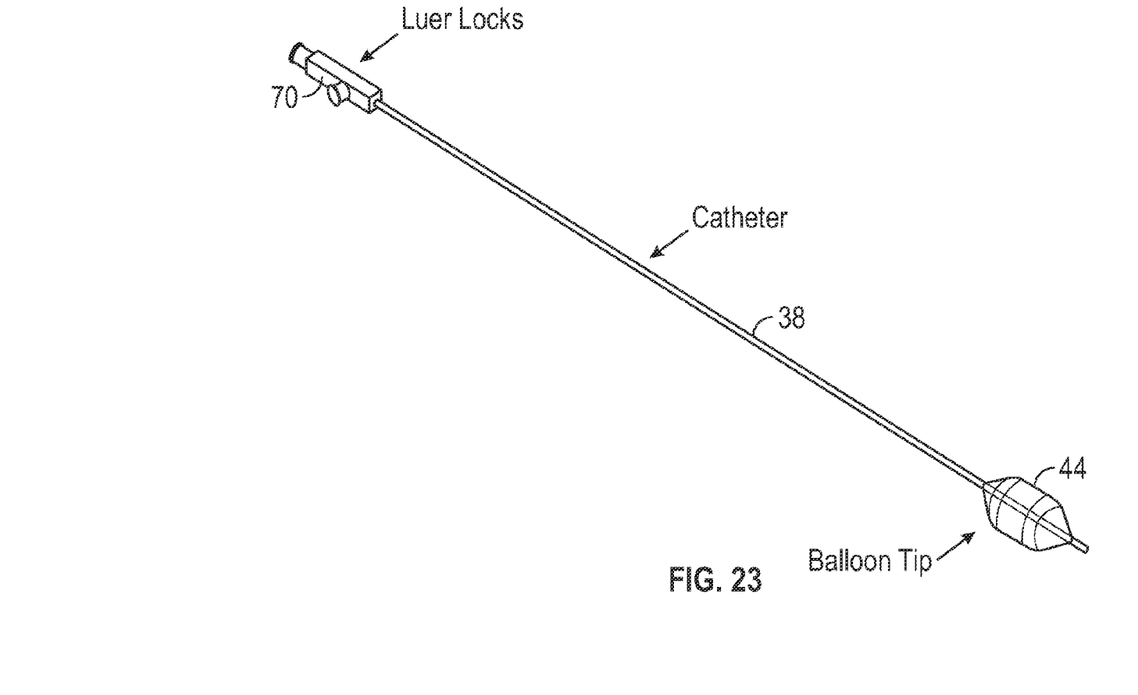
Figure 24:
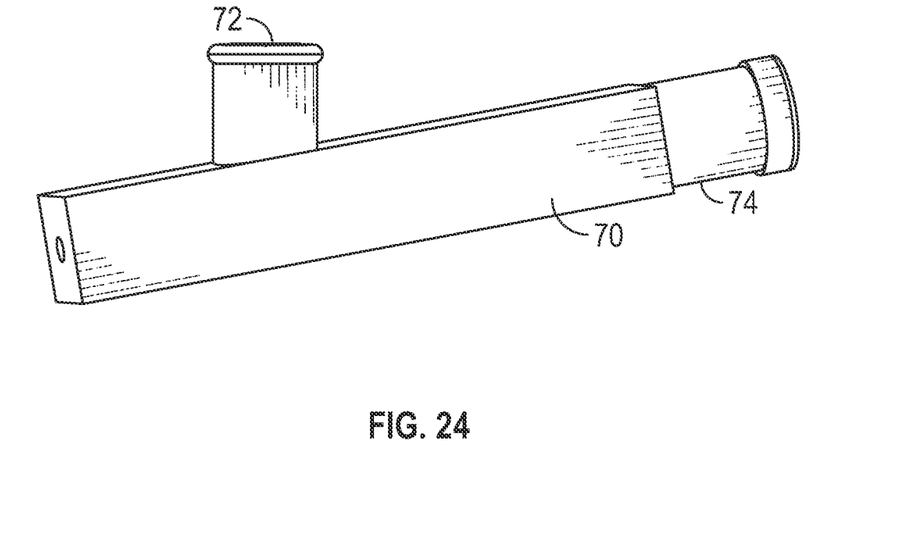
Figure 25:
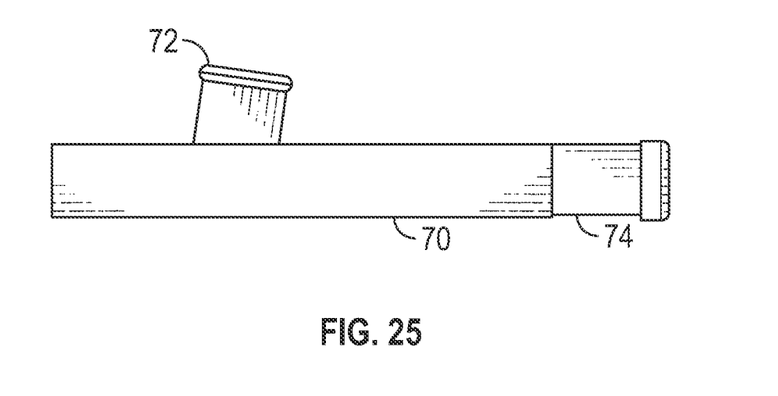
Figure 26:
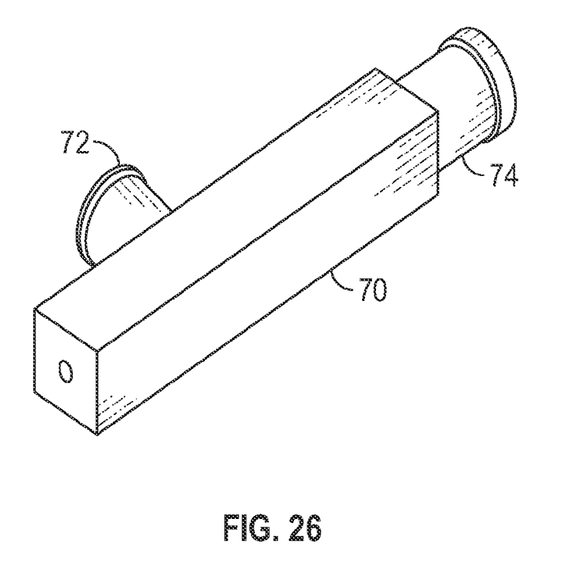

In another embodiment, a cord member 64 is coupled on one end to the balloon 44 (FIG. 19). When the balloon 44 is moved adjacent the aperture 24, the clinician may pull on the cord member 64 which results in the stem portion 38 bending the balloon 44 towards the aperture 24. In yet another embodiment, a second balloon 66 is inserted with the tamponade device (FIG. 20). When the balloon 44 is moved to a position adjacent the aperture 24, the second balloon 66 is inflated causing the tip of the balloon 44 to be elevated through the aperture 24. In yet another embodiment, stem portion 38 is bent in an opposite direction when inserted into the needle 20 such that the bend point 68 advances through the needle 20 prior to the balloon 44 (FIG. 21). The elasticity of the stem portion 38 causes the balloon 44 to rotate about the bend point 68 and through the aperture 24 as the balloon 44 reaches the aperture 24.

Figure 8:
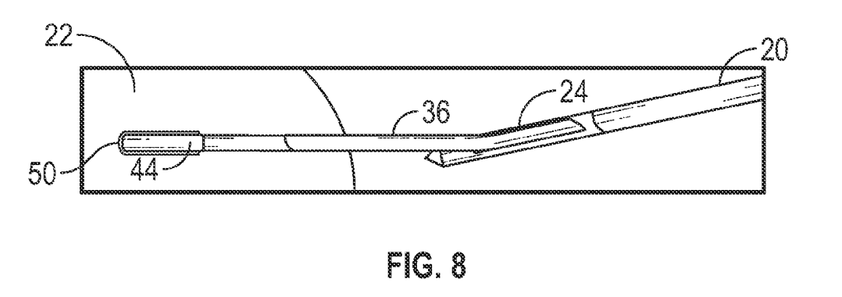
Figure 9:
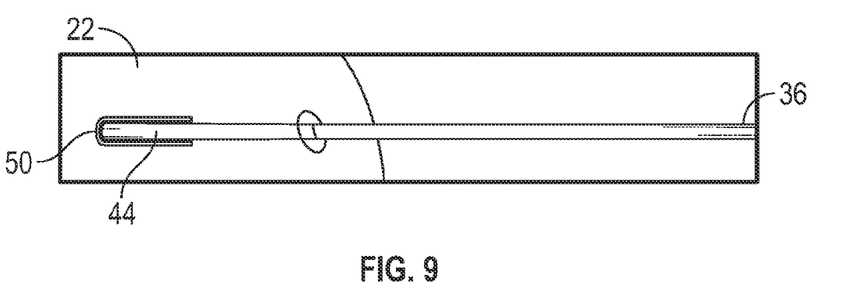
Figure 10:
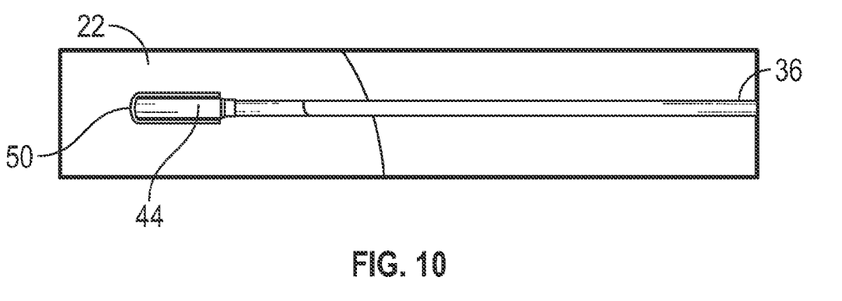
Figure 11:
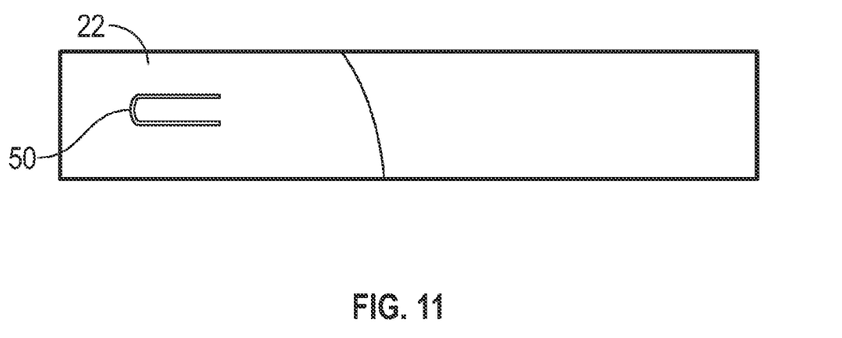

Once the tamponade device 36 has exited the needle 20, the probe 20 is removed over the entire tamponade device 36 in a reverse threading motion (FIG. 8) so that the tamponade device 36 remains inside of the breast 22 (FIG. 9). A pressurized fluid is introduced into the inner bore 45 and the interior portion 46. As the pressure of the fluid is increased, the expandable portion 44 of the tamponade device 36 is inflated forcing the sheath 50 into contact with and against the hemorrhage location within the incision created during the procedure. The pressure from the sheath 50 caused by the expandable portion 44 results in a stoppage of bleeding (FIG. 10). It should be appreciated that the hemorrhage is stopped without or with a reduced amount of external pressure being applied. Once bleeding has stopped, the pressurized fluid is removed causing the expandable portion to deflate while leaving the sheath 50 in the expanded state and in contact with the location where the hemorrhage occurred. In one embodiment, the sheath 50 includes a surgical adhesive that assists in retaining the sheath 50 in the desired location. The stem portion 38 and expandable portion 44 are then removed, while leaving the sheath 50 within the breast 22 (FIG. 11). The sheath 40 degrades over time and is absorbed into the patient's body.

Referring now to FIGS. 22-26, an embodiment incorporating a Luer lock device 70 coupled to the proximal end 40 is shown. The Luer lock device 70 includes two ports 72, 74 in which substances can be inserted or removed from the catheter 38. The first port 72 is used to inflate the balloon 44 and the optional second port 74 is open to the end of the catheter 38. The second port 74 may be used for the introduction of medication or removal of blood from the cavity.

Figure 27:
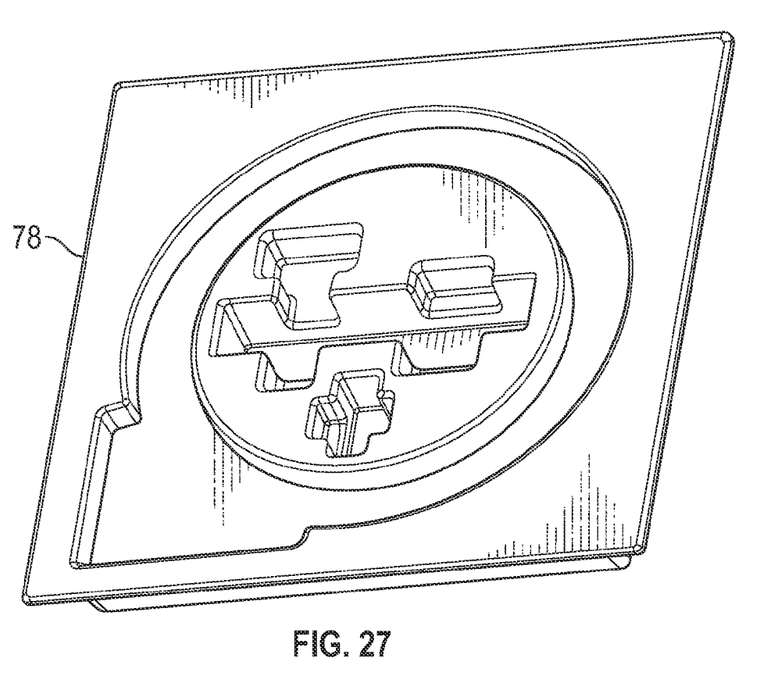
Figure 28:
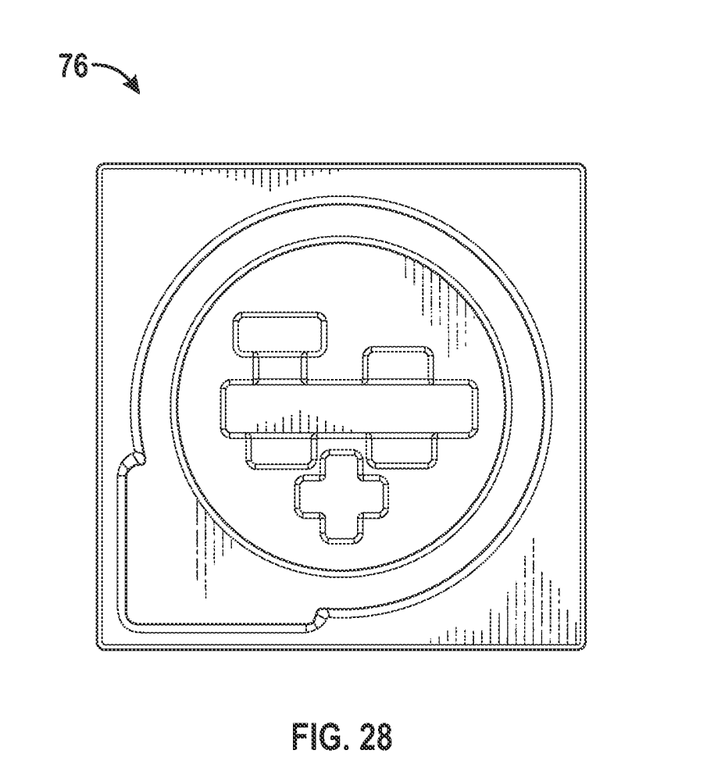
Figure 29:
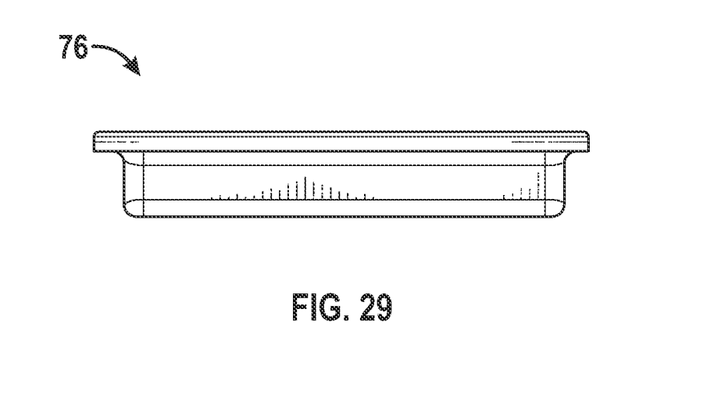

In one embodiment shown in FIGS. 27-29, the tamponade device may be arranged as a kit 76 to facilitate use by the physician during the procedure. The kit 76 consists of a balloon catheter, biodegradable sheath, ejection mechanism for deployment, and a clip all contained within recesses of a single, sterilized package 78. The balloon is the portion that functions to apply pressure to the hemorrhage vessel, causing blood to stop flowing from said vessel. The sheath is located outside the balloon. This sheath functions to separate blood clots from the balloon, allowing the balloon to be removed smoothly once hemorrhage has been stopped. The ejection mechanism is used to eject the balloon catheter from the needle. The scissors and clip are used so that the needle can be completely separated from the patient's body once the needle has been removed from the cavity. The removal is performed by removing the needle from the body over the catheter, inflating the balloon, clipping catheter to maintain pressure inside of balloon, and cutting off the luer lock. Removing the Luer lock allows the needle to slide easily off the end of the catheter.

The tamponade device provides advantages in being able to stop bleeding safely, effectively, and easily. It is expected that the tamponade device will stop bleeding in less than ten minutes for 90% of patients. This is half of the normal amount of time it takes for most (80%) patients who suffered from hemorrhage to stop bleeding. The tamponade device may be able to survive a pressure of 1000 mmHg without leaking or rupturing. The tamponade device provides advantages in working with a large range of breast sized, such as a breast sized AA-J for example. The tamponade device may provide decreased time to implement, such as less than 30 seconds for 90% of users and require less than ten minutes of training for personnel to feel confident using the tamponade device. The ease of use of the tamponade device is such that 95% of users to think its easy to use. It should be appreciated that the tamponade device allows pressure to be directly applied to the hemorrhaging site, it is believed that it will provide advantages in controlling bleeding more quickly than the current standard of practice.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is

1. A tamponade device for stopping hemorrhaging in a surgically created passageway during a biopsy procedure using, the tamponade device comprising:
    a probe having an inner bore;
    a stem portion sized to fit within the inner bore;
    an expandable portion sized to fit within the inner bore, the expandable portion changeable between a first size and a second size wherein the second size is larger than the first size, the expandable portion further being configured to be pressurized in the second size to a pressure level higher than about two times a patient normal systolic blood pressure, wherein the pressure within the expandable portion is substantially uniform about an inner surface of the expandable portion, wherein the pressure level will stop hemorrhaging of a surgically transected blood vessel;
    a sheath having an open first end and a closed second end, the sheath being disposed about and removably coupled to the expandable portion, the sheath sized to fit within the inner bore;
    a surgical sealant disposed on an outer surface of the sheath, the surgical sealant configured in operation to adhere and retain the sheath within the surgically created passageway when the expandable portion is removed from the surgically created passageway; and
    wherein the sheath is made of a biocompatible and bioabsorable material.

2. The device of claim 1 further comprising a plurality of cautery wires disposed about the expandable portion.

3. The device of claim 1 wherein the sheath has a first portion disposed about the expandable portion and a distal end, the distal end having a wall thickness that is larger than the first portion.

4. A device for stopping a hemorrhage within a surgically created passageway during a biopsy procedure comprising:
    a tamponade having a stem portion with an inner bore and an expandable portion, the expandable portion having a substantially hollow interior in fluid communication with the inner bore and having a first outer surface, the expandable portion is inflatable from a first size to a second size at a pressure level, wherein the second size is larger than the first size and the pressure level is about twice the normal patient systolic blood pressure level, wherein the pressure within the expandable portion is substantially uniform across an inner surface of the expandable portion, wherein the pressure level will stop hemorrhaging of a blood vessel;
    a sheath removably coupled to the tamponade, the sheath having an inner portion and a second outer surface, the sheath being disposed over and removably coupled to the first outer surface, wherein the sheath is made from a biocompatible and bioabsorable material; and, a surgical sealant disposed on the second outer surface of the sheath, the surgical sealant configured in operation to adhere and retain the sheath within the surgically created passageway when the expandable portion is removed from the surgically created passageway.

5. The device of claim 4 wherein the sheath has a closed spherical distal end.

6. The device of claim 4 wherein the sheath has a cylindrical shape with a closed substantially flat distal end.

7. The device of claim 4 wherein the sheath has a closed curved and pointed distal end.

8. The device of claim 4 wherein the expandable portion has a length of about 11 millimeters and a diameter of about 2 millimeters.

9. The device of claim 4 wherein the stem portion and the expandable portion are formed as a single contiguous and integral member.

* * * * *